(12) United States Patent
Lo

(10) Patent No.: US 7,189,216 B2
(45) Date of Patent: Mar. 13, 2007

(54) COUPLING STRUCTURE FOR SELF-DESTRUCTION AND SAFETY SYRINGE

(75) Inventor: Pi-Chang Lo, Taipei (TW)

(73) Assignee: Vantex Biotechnology Co., Ltd., Tortola (VG)

( * ) Notice: Subject to any disclaimer, the term of this patent is extended or adjusted under 35 U.S.C. 154(b) by 297 days.

(21) Appl. No.: 10/787,091

(22) Filed: Feb. 27, 2004

(65) Prior Publication Data

US 2005/0192533 A1    Sep. 1, 2005

(51) Int. Cl.
*A61M 5/00*    (2006.01)

(52) U.S. Cl. ...................................... 604/110

(58) Field of Classification Search ................. 604/110, 604/220, 218, 187, 208, 210, 235, 194, 195, 604/196, 198, 263, 240, 181; 128/919
See application file for complete search history.

(56) References Cited

U.S. PATENT DOCUMENTS 5,370,619 A * 12/1994 Rossi ........................... 604/110
5,993,419 A * 11/1999 Lo et al. ...................... 604/110

* cited by examiner

*Primary Examiner*—Nicholas D. Lucchesi
*Assistant Examiner*—Matthew DeSanto
(74) *Attorney, Agent, or Firm*—Troxell Law Office, PLLC

(57) ABSTRACT

A coupling structure for self-destruction and safety syringe including a coupling member is formed on a front-end of a self-destruction and safety plunger. Upon the plunger being pushed in a hollow barrel until the plunger cannot be pushed any further, a lengthways long slit together with a coupling member are able to deform and thus provide for an allowance spacing when forcedly squeezed, and thereby enables the coupling member to easily and accurately form a complete coupling.

7 Claims, 10 Drawing Sheets

COUPLING STRUCTURE FOR SELF-DESTRUCTION AND SAFETY SYRINGE

BACKGROUND OF THE INVENTION (a) Field of the Invention

The present invention relates to a coupling structure for self-destruction and safety syringe, and more particularly to the coupling structure wherein a lengthways long slit is configured in an area of a coupling member, and utilized to provide a deformation allowance for when forcedly squeezing a coupling, and implemented in the coupling structure of a plunger of the self-destruction and safety syringe.

(b) Description of the Prior Art

Infection from medical treatment is an intolerable issue, and overwhelming majority of channels of infection for many virulent diseases is through infection of blood. Therefore, one-time usage of medical treatment appliances or because of individual requirements is clearly of great importance.

Thus prior to the present invention the inventor invented two configurations for a syringe including a self-destruction syringe and a safety syringe, moreover successively acquired patents for same in the United States of America, Taiwan, and China, having patent numbers U.S. Pat. Nos. 6,488,657 B1, US 5,993,419, ZL02239125.8, 202056, respectively, objective of which was to provide a traditional syringe with a configuration that only allowed single-usage, and did allow for recycling after the syringe was discarded, and with such a configuration to realize complete eradication of infection from needles used in medical treatment.

In light of the aforementioned related patents, a primary structural characteristic of the self-destruction and the safety syringe is in a coupling member configured on a plunger, which provides for coupling to a retaining ring of a needle holder. Upon the plunger being pulled back, a plug member disengages from the plunger and a rubber bulb within the self-destruction syringe, thereby enabling the syringe to lose an airtight vacuum state, and thus losing suction functionality for the syringe to be reused. Furthermore, regarding the safety syringe, the needle and the needle holder integral therewith are received within a hollow barrel, thereby achieving functionality of a safety design, wherewith medical personnel are prevented from being pricked by the needle.

Hence, coupling action of the coupling member is a cardinal key of the self-destruction syringe and the safety syringe, and therefore structural design of the coupling member is of particular importance.

SUMMARY OF THE INVENTION

A primary objective of a coupling structure for self-destruction and safety syringe of the present invention is to provide the coupling structure that can be implemented in the self-destruction and safety syringe, and thereby furnish a structural design that can accommodate syringes of differing capacity. The coupling structure primarily comprises a lengthways long slit configured in an area of a coupling member, and which provides for a forcedly squeezed deformation allowance spacing when coupling, thereby enabling the coupling member to easily and accurately form a mutually coupling with a retaining ring of a needle holder. Therefore, such a coupling structure allows for implementation in syringes of comparatively larger or relatively smaller capacity, whereby because a coupling force required by barrels of comparatively larger capacity is correspondingly large, and barrels of smaller capacity, which thus have a corresponding space restriction, thereby require a greater need for a precise coupling connection.

To enable a further understanding of the said objectives and the technological methods of the invention herein, the brief description of the drawings below is followed by the detailed description of the preferred embodiments.

DETAILED DESCRIPTION OF THE PREFERRED EMBODIMENTS

Figure 1A:
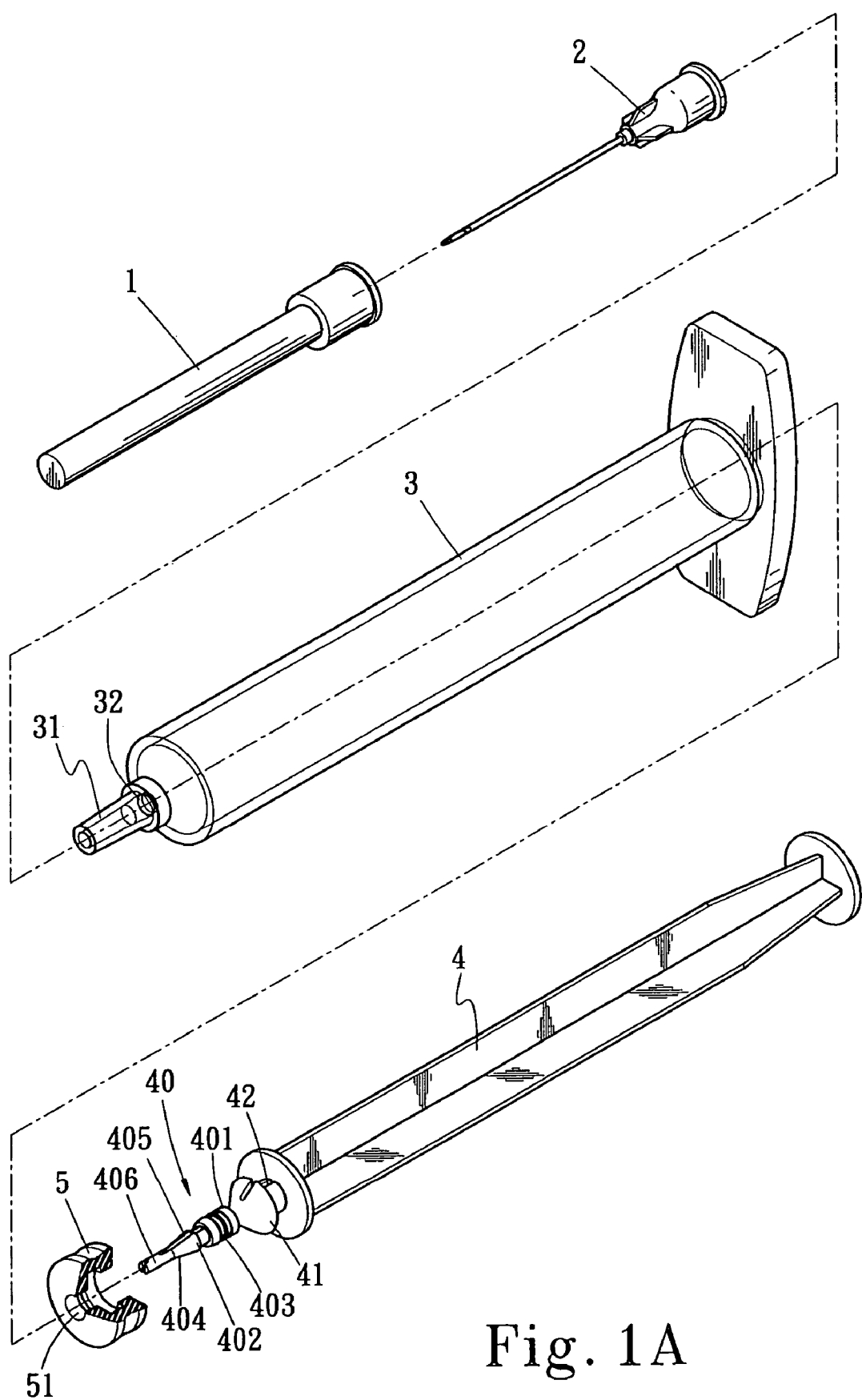
FIG. 1A shows an exploded elevational view of a self-destruction syringe according to the present invention.
Figure 1B:
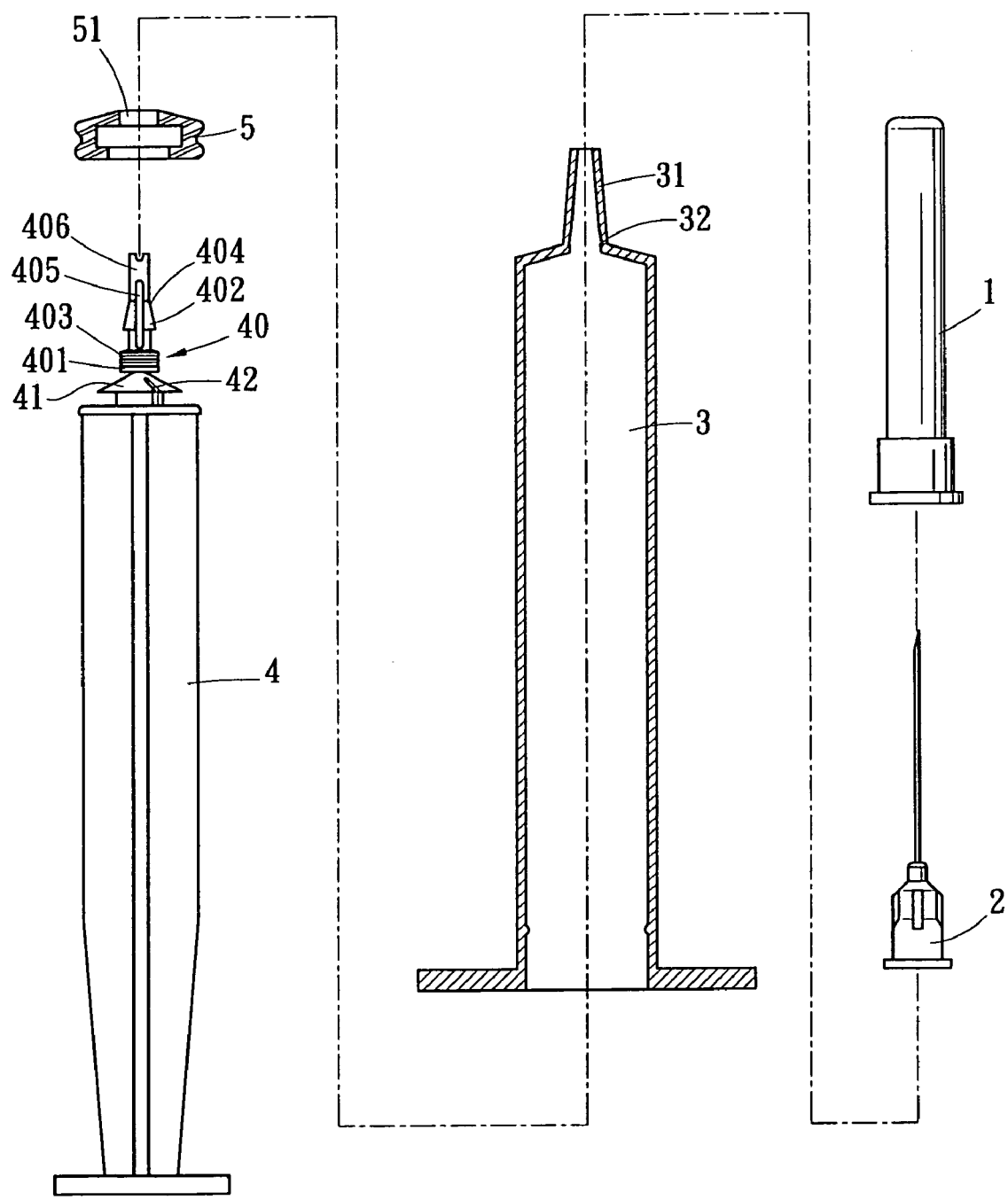
FIG. 1B shows a front view of the self-destruction syringe according to the present invention.
Figure 2:
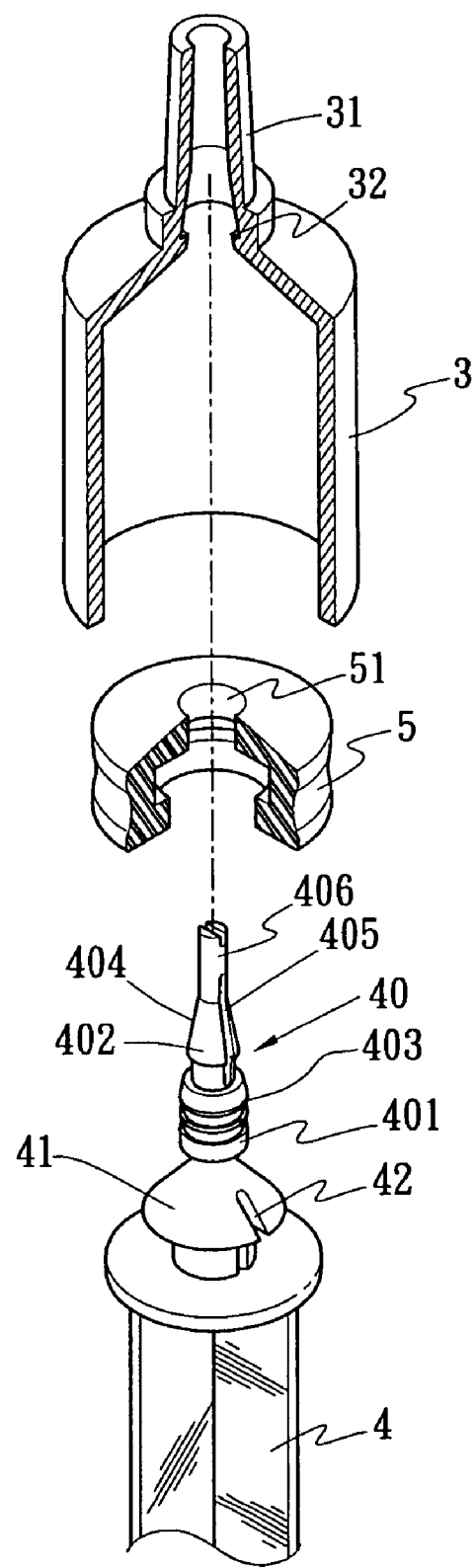
FIG. 2 shows a partial exploded elevational view of characteristics of the self-destruction syringe according to the present invention.

Referring to FIGS. 1A, 1B and 2, which show an embodiment of a self-destruction syringe of the present invention, wherein structure of the self-destruction syringe is primarily configured to comprise a sleeve 1, a needle base 2, a hollow barrel 3, a plunger 4 and a rubber bulb 5. Wherein the hollow barrel 3 is so configured to provide for containing the rubber bulb 5 and the plunger 4. A retaining ring 32 is configured interior of a front-end connecting holder 31, and which provides for a coupling member 402 of a plug member 40 of the plunger 4 to be retained therein. A front-end of the plunger 4 is adapted to form a coupling head 41, which provides for coupling with the rubber bulb 5. An air escape slit 42 is defined in a side of the coupling head 41, whereby the air escape slit 42 is designed as an air escape configuration for when the plug member 40 disengages from the coupling head 41, and thereby disenables the hollow barrel 3 from maintaining an airtight vacuum, and thus realizes a safety self-destruction structure.

The plug member 40 of a frontal section of the coupling head 41 is adapted to form the coupling member 402, a stem member 406, a plurality of hermetic sealing rings 403 and a stop-leakage ring 401. Wherein a lengthways long slit 405 is defined on the stem member 406 and the coupling member 402. When the plunger 4 is pushed forward until can no longer be pushed, thereat the plug member 40 of the plunger 4 engages with the retaining ring 32, whereupon the coupling member 402 is forcedly squeezed to couple therein, at such time the long slit 405 thus primarily provides for allowance spacing. A perforation 51 is defined center of the rubber bulb 5, and which provides for the plug member 40 to penetrate. When the aforementioned hermetic sealing rings 403 and the stop-leakage ring 401 are embedded within the perforation 51, a stop-leakage hermetically sealed configuration is thereupon formed.

Figure 3:
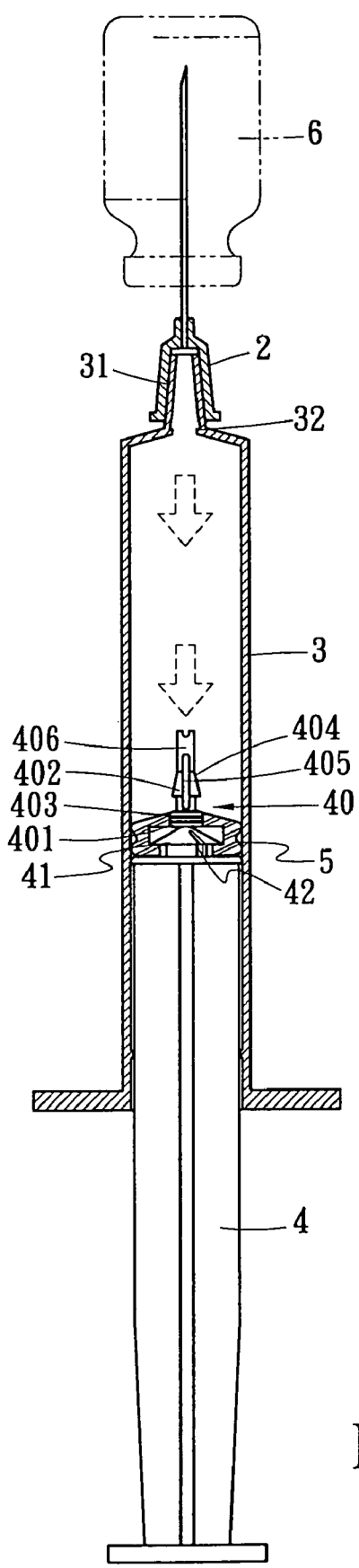
FIG. 3 shows a cross sectional schematic view depicting drawing out of medicament according to the present invention.

Referring to FIG. 3, which shows the present invention during usage, whereby operating procedure is exactly same as operating method of a conventional hypodermic syringe. First, as with the conventional syringe, a needle is inserted into a medicine bottle 6 containing an injection medicament. Because the rubber bulb 5 of the plunger 4 realizes a vacuum state with an inner wall of the hollow barrel 3, therefore when the plunger 4 is pulled back from the hollow barrel 3, the medicament is drawn out of the medicine bottle 6 and into the hollow barrel 3, and thus is in a standby state ready for injection. After slight adjustment by medical personnel, the syringe is ready to carry out an injection. The operating procedure as disclosed completely complies with traditional medical practices and approved regulations for use of the hypodermic syringe, and thus there is no need for additional training on operating usage.

Figures 4A, 4B, 4C:
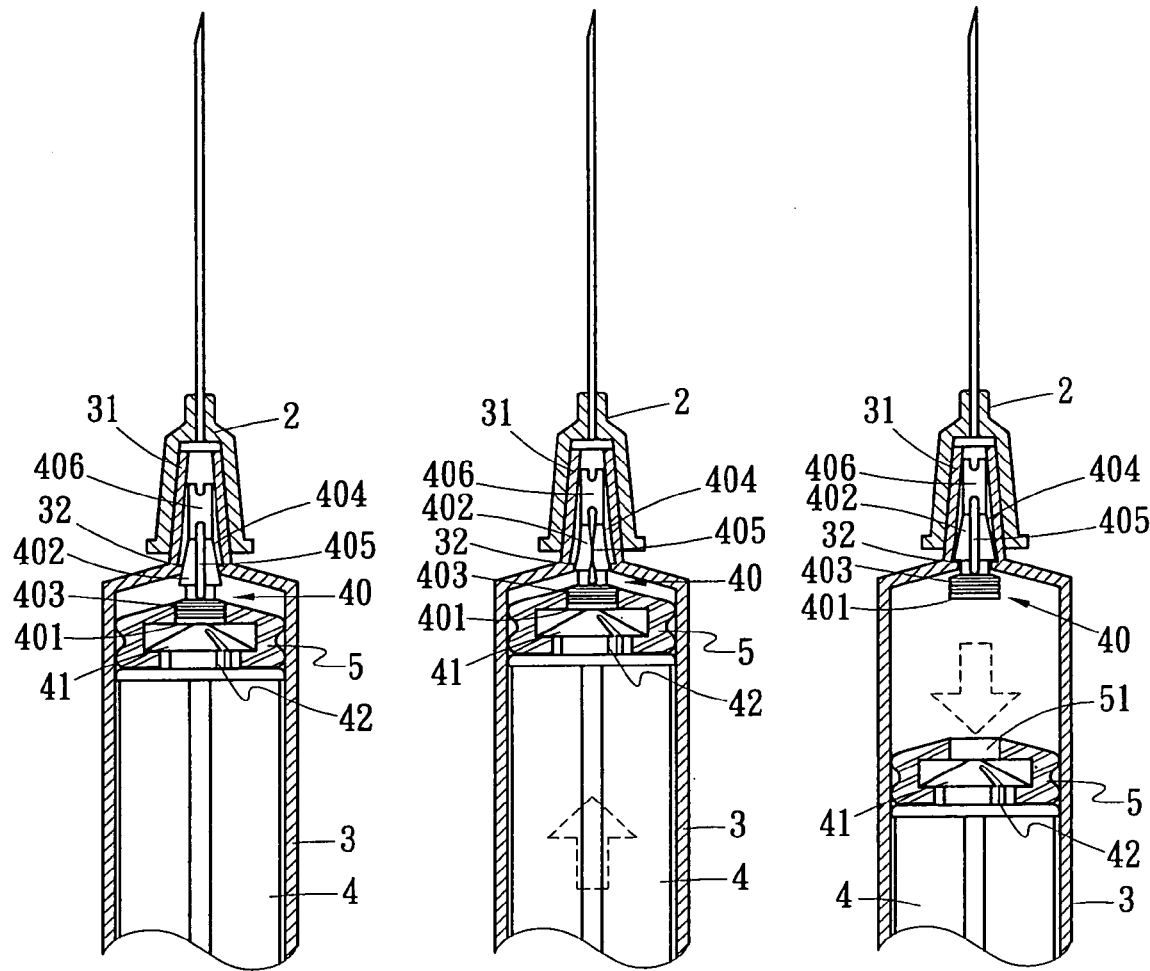
FIG. 4A shows a first drawing of a cross sectional view of the self-destruction syringe in usage according to the present invention.
FIG. 4B shows a second drawing of a cross sectional view of the self-destruction syringe in usage according to the present invention.
FIG. 4C shows a third drawing of a cross sectional view of the self-destruction syringe in usage according to the present invention.

Referring to FIGS. 4A, 4B and 4C, upon the medical personnel pressing on the plunger 4, a front push of the vacuum formed by the rubber bulb 5 thereby injects the medicament into a body of a patient through the needle. When the rubber bulb 5 front reaches a bottom of the hollow barrel 3, the coupling member 402 thereupon forms an appropriate resistive force within an injection orifice 33. Thus the injection procedure is completed, and design of the stem member 406 enables complete injection of the medicament without leaving a trace of the medicament within the hollow barrel 3 (see FIG. 4A). Thereupon, the medical personnel can withdraw the needle from the patient.

However, in order to prevent reuse of the hollow barrel 3, after the needle has been withdrawn from the body of the patient, the plunger 4 can be further pressed forward (see FIG. 4B), thereby enabling the coupling member 402 of the plug member 40 to embed into the retaining ring 32 of the hollow barrel 3. At moment of forming a coupling, resilience of a conical surface of an inclined guide face 404 of the coupling member 402, together with the lengthways long slit 405 are able to deform and thus provide for the allowance spacing when forcedly squeezed, and thereby enables the coupling member 402 to even more easily and accurately form a mutual coupling with the retaining ring 32. Thus the stem member 40 is completely coupled within the retaining ring 32, forming a self-destruction condition.

Notwithstanding, after an operator has completed the injection and completed coupling of the syringe as aforementioned, the plunger 4 must be pulled back. Because a coupling force of the coupling member 402 and the retaining ring 32 is greater than strength of a secure fixing of the plug member 40 and the coupling head 41, thus the plug member 40 and the coupling head 41 break apart (see FIG. 4C). After pulling back the plunger 4, the plug member 40 is coupled to the retaining ring 32 of the hollow barrel 3, and backward pulling of the plunger 4 and the rubber bulb 5 enables the central perforation 51 of the rubber bulb 5 to assume an open state.

Figure 5:
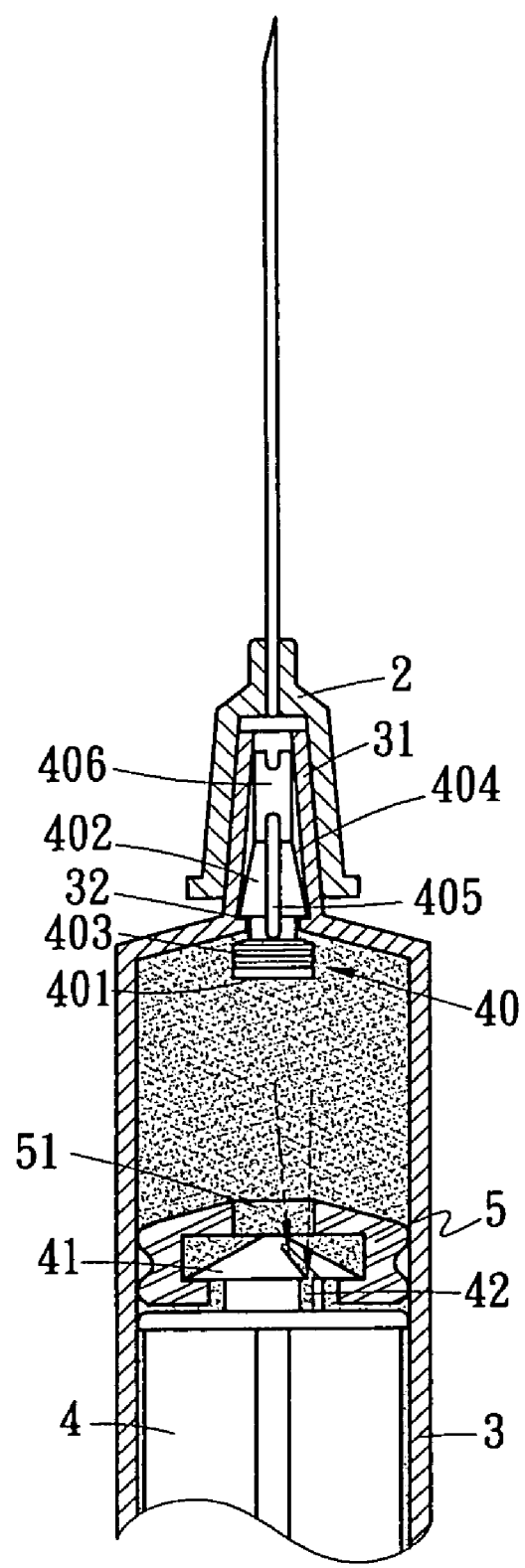
FIG. 5 shows a cross sectional view of the self-destruction syringe in a lost-vacuum state according to the present invention.

According to the aforementioned, and referring to FIG. 5, after completion of the injection procedure, and upon pulling back the plunger 4, the coupling member 402 breaks apart from the coupling head 41 of the plunger 4, and at the same time disengages from the perforation 51 of the rubber bulb 5, thereby enabling the perforation 51 to assume a through-passage state connecting with the air escape slit 42. With such a configuration between the rubber bulb 5 and the plunger 4, because of the disengaging of the plug member 40, an air vent so produced disenables the hollow barrel 3, the plunger 4 and the rubber bulb 5 configuration from maintaining an airtight state, and thus loses functionality to draw out and inject the medicament. Hence, when a user pulls and pushes the plunger 4, air thus escapes from the air escape slit 42 of the perforation 51 and the coupling head 41, and disenables the rubber bulb 5 and the hollow barrel 1 from reforming a hermetic sealed space, thereby disallowing the operator from reusing the present invention to implement drawing out or injecting of injection medicament. The aforementioned disclosure has been taken in consideration as a safety self-destruction aspect, because the drawing out and injection of the medicament by the syringe needs an air tight structural space to implement such, thus the present invention prevents the hollow barrel 3 from being reused, thereby eradicating completely occurrence of infection from medical treatment.

Figure 6:
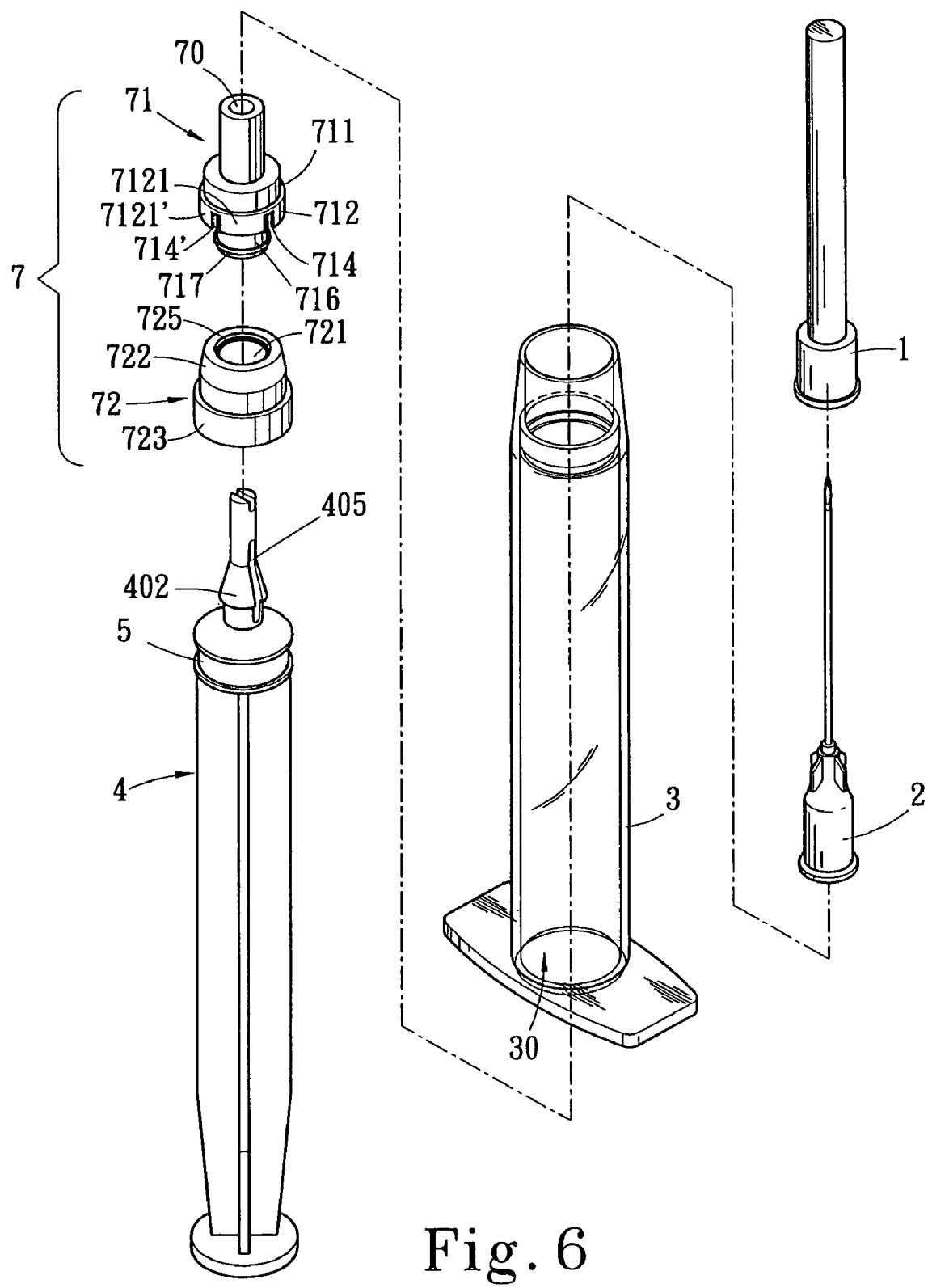
FIG. 6 shows an exploded elevational view of a safety syringe according to the present invention.
Figure 7:
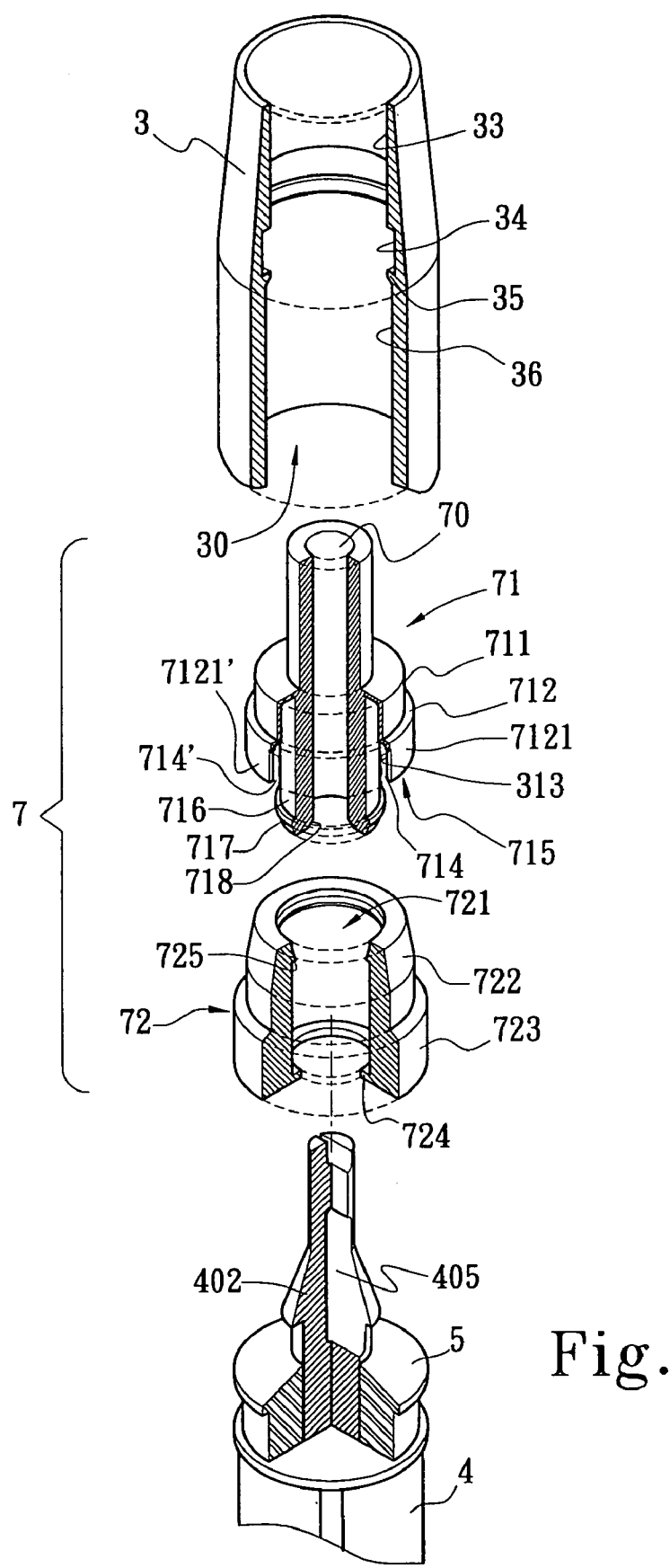
FIG. 7 shows a partial exploded elevational view of the safety syringe according to the present invention.

Referring to FIGS. 6 and 7, which show a configuration of the safety syringe of the present invention, wherein the safety syringe is structured to comprise the sleeve 1, the needle base 2, the barrel 3, a secure fixing holder 7, the plunger 4 and the rubber bulb 5. Moreover, the secure fixing holder 7 comprises a needle holder 71 and a coupling holder 72. Wherein the barrel 3 is a hollow tube, and formed as a receptacle chamber 30. A drop annular groove 34 of comparatively larger caliber is defined in an inner wall of a front-end caliber of the receptacle chamber 30. The annular groove 34 provides for coupling of the needle holder 71 of the secure fixing holder 7, and the needle holder 71 provides for fixedly connecting the needle base 2 therein. Moreover, a perforation 70 is defined in a central position of the secure fixing holder 7, and provides for the medicament to be injected into the needle 2. An upper-step ring 711 and a lower-step ring 712 are configured on a lower section of the needle holder 71, wherein diameter of the lower-step ring 712 is greater than that of the upper-step ring 711. Moreover, a plurality of allowance slits 714, 714' are annular distributed and defined on the lower-step ring 712 thereof, and therefrom a plurality of spring leaves 7121, 7121' are thus formed. An inner annular receptacle groove 715 formed by the lower-step ring 712 protruding out more than the upper-step ring 711, and structural design of the allowance slits 714, 714' enable the spring leaves 7121, 7121' to be provided with a superior resilient allowance. When the secure fixing holder 7 and the barrel 3 are joined, the spring leaves 7121, 7121' of the lower-step ring 712 are utilized to couple with the annular groove 34, and thereupon completes a fixed connection thereof. An inner stem 716 downwardly extends from the inner annular receptacle groove 715 of a lower section of the needle holder 71, and the inner stem 716 provides for penetrating and engaging with a receptacle recess 721 of the coupling holder 72. In addition, an upper coupling ring 717 on an extremity of the inner stem 716 mutually couples with a lower coupling ring 725 of the coupling holder 72, thereby confining movement of the coupling holder 72 to a straight line on the inner stem 716. A top section of the coupling holder 72 circumferentially forms a conical surface 722, and an annular holder 723 is configured on the conical surface 722. Wherein, when the coupling holder 72 and the needle holder 71 engage, the conical surface 722 provides for forming a resistance against the inner annular receptacle groove 715 of the needle holder 71, and an inner wall of the lower-step ring 712 and the spring leaves 7121, 7121' thereby enable complete engagement of the coupling holder 72 and the needle holder 71. Furthermore, the annular holder 723 functioning in coordination with a lower inner wall of the barrel 3 can thereby ensure accuracy in assembling the secure fixing secure fixing 7 and the barrel 3.

Figure 8A:
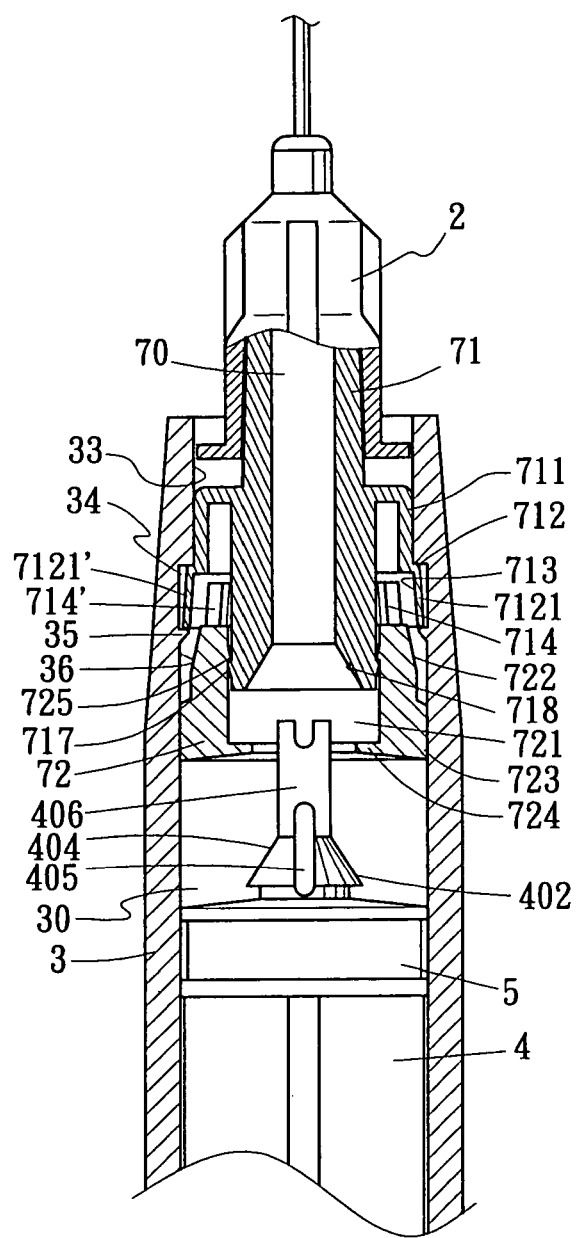
FIG. 8A shows a first drawing of a cross sectional view of the safety syringe in usage according to the present invention.
Figure 8B:
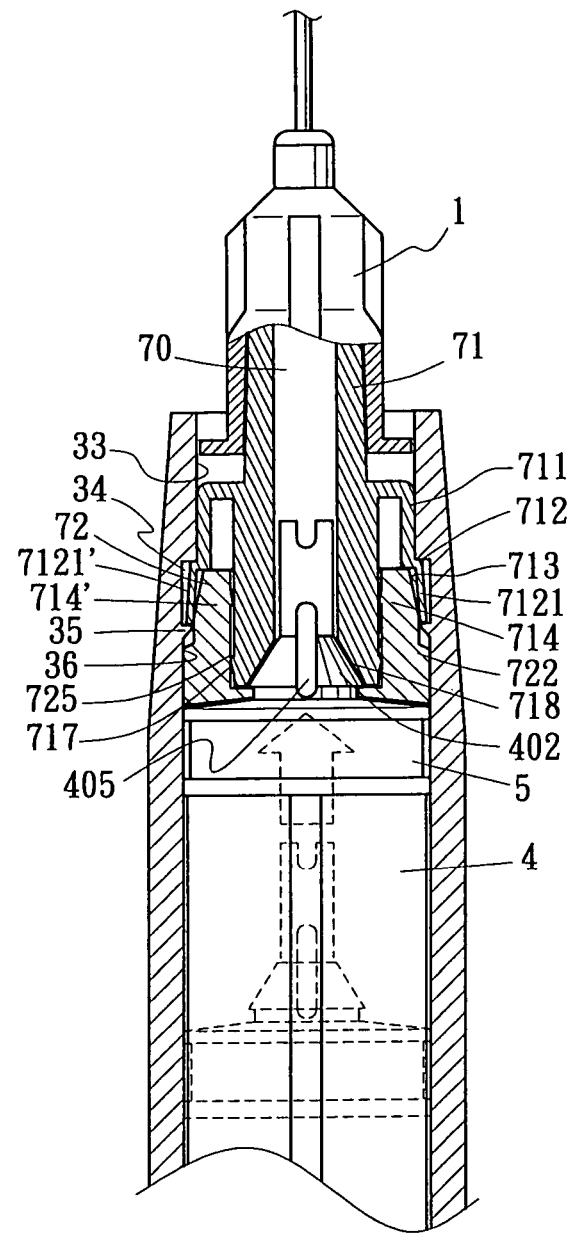
FIG. 8B shows a second drawing of a cross sectional view of the safety syringe in usage according to the present invention.

In addition, the conical coupling member 402 and the covering rubber bulb 5 are configured on an end of the plunger 4, wherein, the coupling member 402 embeds into a retaining ring 724 configured in a bottom of the coupling holder 72, thereby forming a structural configuration which only allows pushing in one-way, and inability to pull out. However, to eliminate any shortcomings and achieve objectives as disclosed, the lengthways long slit 405 is configured on an area of the coupling member 402 of the present invention, and referring to FIG. 8A, upon coupling, the lengthways long slit 405 together with the retaining ring 724 are able to deform and thus provide for the allowance spacing when forcedly squeezed, and thereby ensure the coupling member 402 maintains a secure mutual coupling with the retaining ring 724. Furthermore, such a configuration allows for accommodation of a comparatively larger coupling force required by barrels of comparatively larger capacity, as well as barrels of smaller capacity, which thus have a corresponding space restriction, thereby require a greater need for a precise coupling connection.

Figure 9:
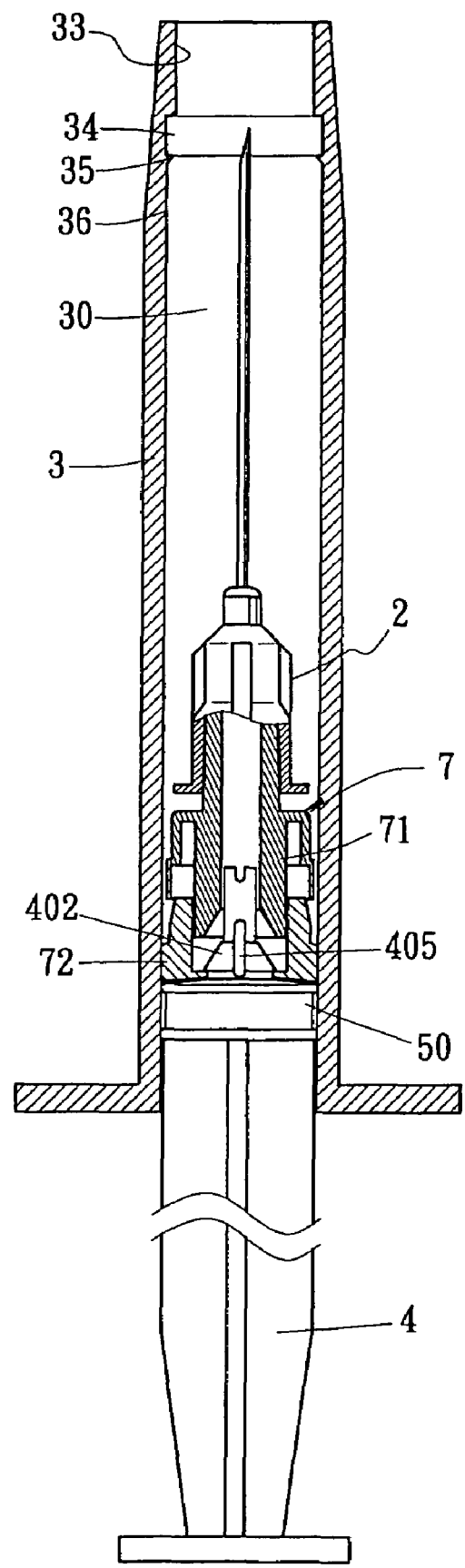
FIG. 9 shows a cross sectional schematic view of containment in a barrel of the safety syringe according to the present invention.

Referring to FIGS. 7 and 9, the plunger 4 is pushed forward until engagement with the retaining ring 724 of the coupling holder 72, thereat disenabling disengagement from the secure fixing holder 7, and when the plunger 4 is pulled back and thus forces the spring leaves 7121, 7121' of the needle holder 71 to disengage from coupling with the support ring 35 of the annular groove 34, the needle base 2 and the secure fixing holder 7 are thereby enabled to be retracted back within the receptacle chamber 30 of the barrel 3. Such a configuration realizes a safety consideration that prevents the medical personnel from being pricked by the needle.

In conclusion, it is of course to be understood that the embodiments described herein is merely illustrative of the principles of the invention and that a wide variety of modifications thereto may be effected by persons skilled in the art without departing from the spirit and scope of the invention as set forth in the following claims.

What is claimed is:

1. A self-destructive safety syringe comprising:
   a) a hollow barrel having a front-end connecting holder having a retaining ring located on an interior thereof; and
   b) a plunger having a plug member movable between slidable and locked positions and having:
      I) a coupling member having an inclined guide face having an exterior surface inclining outwardly when moving in a direction from a first end to a second end of the plunger;
      ii) a stem member located on the first end of the plunger and extending outwardly from the inclined guide face, the stem member is selectively inserted into the front-end connecting holder; and
      iii) a lengthwise long slit located in a side of the stem member and the coupling member, the lengthwise long slit is spaced apart from the first end of the plunger;
   wherein, when the plunger is located in the slidable position, the inclined guide face of the coupling member is spaced apart from the retaining ring of the front-end connecting holder, the plug member is slidable along the interior of the hollow barrel, and when the plunger is located in the locked position, the stem member and the coupling member are inserted into the front-end connecting holder, the retaining ring engaging the inclined guide face and fixing the stem member and the coupling member in the front-end connecting holder.

2. The self-destructive safety syringe according to claim 1, further comprising a rubber bulb having a peroration, the plug member is inserted through the perforation.

3. The self-destructive safety syringe according to claim 2, wherein the plunger includes a coupling head having an air escape slit located in a side thereof.

4. The self-destructive safety syringe according to claim 1, wherein the lengthwise long slit is movable between open and non-open positions, when the plunger is located in a position selected form a group consisting of the slidable position and the locked position, the lengthwise long slit is located in the open position, and when the plunger is moving from the slidable position to the locked position, the lengthwise long slit is located in the non-open position as the coupling member is forced past the retaining ring.

5. The self-destructive safety syringe according to claim 1, wherein the lengthwise long slit extends parallel with a length of the plunger.

6. The self-destructive safety syringe according to claim 1, wherein the stem member has an outer diameter smaller than an outer most diameter of the coupling member.

7. The self-destructive safety syringe according to claim 1, wherein the lengthwise long slit extends across a length of the inclined guide face.

* * * * *